US009781869B2

(12) United States Patent
Molnar et al.

(10) Patent No.: US 9,781,869 B2
(45) Date of Patent: Oct. 3, 2017

(54) ENERGY CONVERSION DEVICE

(71) Applicants: Marianna Juhaszne Molnar, Miskolc (HU); Janos Juhasz, Miskolc (HU)

(72) Inventors: Marianna Juhaszne Molnar, Miskolc (HU); Janos Juhasz, Miskolc (HU)

( * ) Notice: Subject to any disclaimer, the term of this patent is extended or adjusted under 35 U.S.C. 154(b) by 0 days.

(21) Appl. No.: 15/037,307

(22) PCT Filed: Nov. 17, 2014

(86) PCT No.: PCT/HU2014/000106
§ 371 (c)(1),
(2) Date: May 17, 2016

(87) PCT Pub. No.: WO2015/075491
PCT Pub. Date: May 28, 2015

(65) Prior Publication Data
US 2016/0295753 A1    Oct. 6, 2016

(30) Foreign Application Priority Data
Nov. 19, 2013    (HU) ................................. 1300211 U

(51) Int. Cl.
H01Q 19/00    (2006.01)
H01Q 17/00    (2006.01)
H05K 5/02    (2006.01)
H05K 9/00    (2006.01)

(52) U.S. Cl.
CPC .................................. H05K 9/0052 (2013.01)

(58) Field of Classification Search
USPC .... 343/700 R, 762; 250/505.1, 507.1, 515.1, 250/522.1, 526
See application file for complete search history.

(56) References Cited

U.S. PATENT DOCUMENTS

| | | | | |
|---|---|---|---|---|
| 5,336,894 A | * | 8/1994 | Ellers | ...................... G01J 5/522 250/504 R |
| 7,193,577 B2 | * | 3/2007 | Malecki | ................... A61N 1/16 343/767 |
| 7,288,777 B2 | * | 10/2007 | Partlo et al. | ........... B82Y 10/00 250/504 R |
| 7,288,778 B2 | * | 10/2007 | Partio et al. | ........... B82Y 10/00 250/504 R |

(Continued)

Primary Examiner — Bernard Souw
(74) Attorney, Agent, or Firm — Joseph G. Seeber

(57) ABSTRACT

The present invention relates to energy conversion device which contains one or more collection units (10) suitable for receiving environmental energy as well as a conversion unit (30) in an electrically conducting connection with the collection unit (10) with the help of a cable (20), at least one of the collection units (10) is formed by a set of metal material pipe members (11), while the conversion unit (30) has a condenser part-unit (32) consisting of metal armored plates (32a, 32a') separated from each other by a gap (T) and located in the cover (31), as well as a frequency-setting part-unit (33) cooperating with the condenser part-unit (32), where the frequency-setting part-unit (33) has a reception space (35) located within the cover (31) of the conversion unit (30) and enclosed by a delimiting shell (34) in the vicinity of the condenser part-unit (32) and a charge (40) located in the reception space (35), and the charge (40) contains an organic component and an inorganic component distributed in a carrier medium (36).

20 Claims, 1 Drawing Sheet

(56) References Cited

U.S. PATENT DOCUMENTS

| | | | |
|---|---|---|---|
| 7,309,871 B2* | 12/2007 | Bowering | B82Y 10/00 250/504 R |
| 7,392,011 B1* | 6/2008 | Jacomb-Hood | H01Q 1/288 342/368 |
| 7,893,414 B2* | 2/2011 | Larsen et al. | G21F 1/00 250/505.1 |
| 7,923,709 B1* | 4/2011 | Chen et al. | G21F 1/125 250/505.1 |
| 8,492,738 B2* | 7/2013 | Ueno et al. | G03F 7/70033 250/492.1 |

* cited by examiner

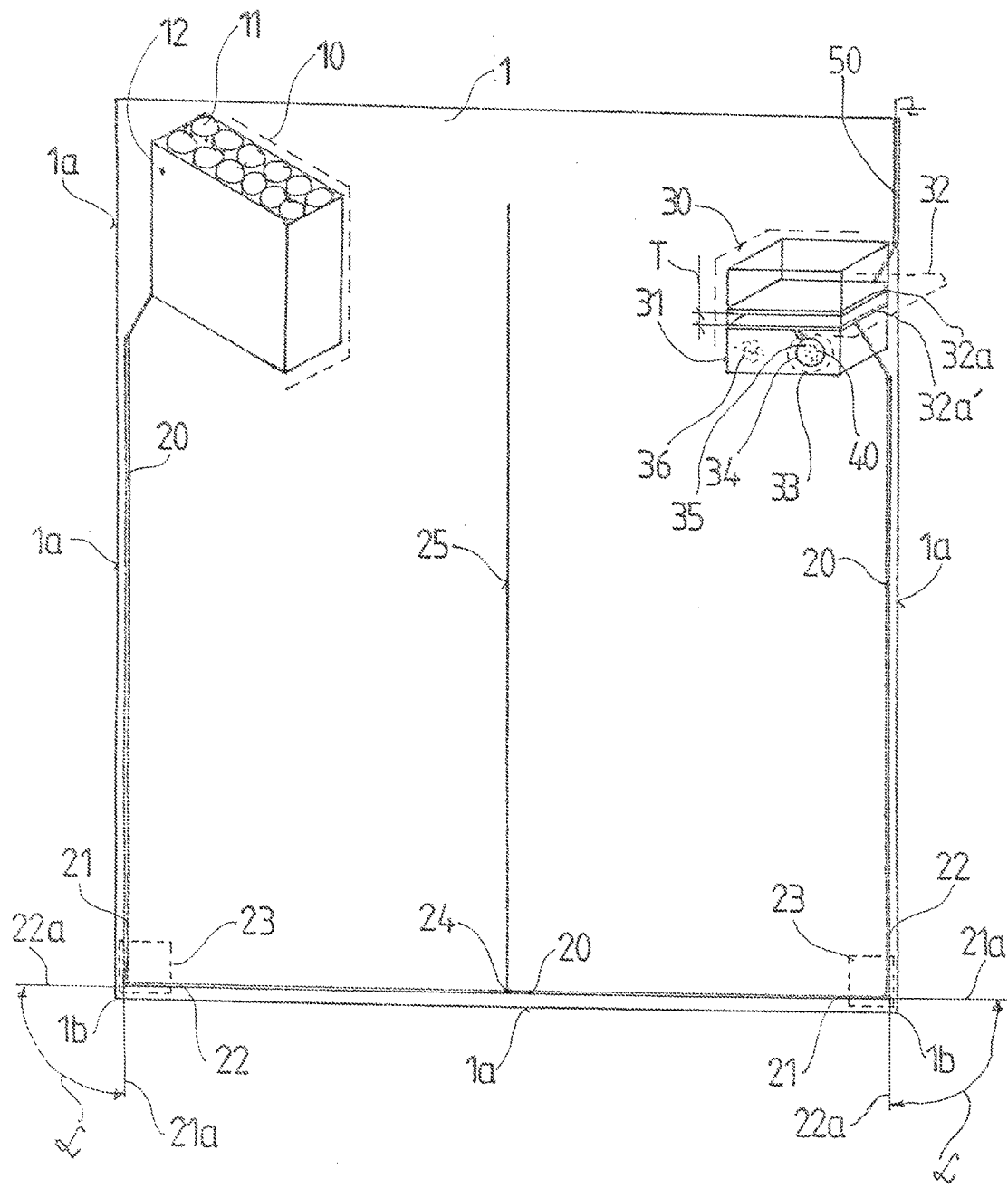

ENERGY CONVERSION DEVICE

The subject of the invention relates to an energy conversion device which contains one or more collection units suitable for receiving environmental energy as well as a conversion unit in an electrically conducting connection with the collection unit with the help of a cable, at least one of the collection units is formed by a set of metal material pipe members, while the conversion unit has a condenser part-unit consisting of metal armoured plates separated from each other by a gap and located in the cover, as well as a frequency-setting part-unit cooperating with the condenser part-unit, where the frequency-setting part-unit has a reception space located within the cover of the conversion unit and enclosed by a delimiting shell in the vicinity of the condenser part-unit and a charge located in the reception space, and the charge contains an organic component and an inorganic component distributed in a carrier medium.

With the spreading of the use of various electronic devices using radio frequency data transmission, e.g. mobile telephones, WiFi equipment, wireless short-range communication devices, etc. electromagnetic environmental pollution today is at an increasingly greater scale. Research and examinations have shown that an exaggerated radiation load influences the feeling of well-being and the life-rhythm of some living organisms, including people, and in a more serious case it even has a health-damaging effect.

Several solutions have been created to overcome this problem in which they endeavour to moderate the electromagnetic radiation arriving from the environment, or even exclude it from the protected area, using electrically conducting and shielding auxiliary devices.

A solution serving to moderate the radiation components harmful to health in the electromagnetic fields of buildings may be seen in, for example, patent specification registration number HU 226.648. The essence of this is that the delimiting structural elements of the building are supplemented with metal grids, special paint and other devices with a shielding effect with various structural characteristics, and the electric circuit set up from these conducting elements, coupled with discrete electrical elements, is connected to earth potential, in this way attempting to exclude the electromagnetic radiation, or at least reduce it in the building part, e.g. apartment, to be protected.

The disadvantage of the solution, however, is that the installation of the devices promoting protection involves a significant investment of physical labour, large-scale changes have to be carried out on the space delimiting elements of the building, which is time-consuming and restricts the activities of the users for an extended period of time, furthermore, the installation of the protection involves large costs.

A simpler and less costly solution is offered by the solution presented in utility model specification registration number HU 2830. The essence of this is that the damaging electromagnetic radiation is "trapped" with the help of a collection unit and is then conducted through a conversion unit. On the effect of the physical and chemical processes taking place in the conversion unit, the electromagnetic radiation is transformed, and so its health-damaging effect does not appear either.

The deficiency of this solution is that, on the one hand, the conversion unit of the energy conversion device demands the connection of several difficult-to-handle structural elements in order for it to be able to exert its effect, therefore, its positioning also continues to be difficult. A further disadvantage is that the effectiveness of the conversion unit is less than that desired as a consequence of the form of the frequency-setting part-unit and its charge.

Our aim with the arrangement according to the invention was to overcome the deficiencies of the known, installed devices providing protection against electromagnetic radiation and to create a construction that is built from a small number of simple structural elements, that may be installed easily and quickly, and, a result of the form of the conversion unit, that is able to absorb the electromagnetic radiation with better efficiency than the versions already in use.

The basis of the idea behind the invention was formed by the results of the most recent research carried out by professor Dr Teruo Higa, through which such microorganisms became known of that in the appropriate environment are able to utilise the energy available in hazardous materials and radiation in the interest of maintaining their existence and therefore regenerate the environment by essentially "absorbing" it. Also by combining appropriate microorganisms self-sustaining micro-ecosystems may be established that also make it possible to use the energy carried in electromagnetic radiation.

The recognition that led to the structure according to the invention was that if the collection unit known of in itself is connected to the conversion unit in an unusual way, with a cable made from a unique alloy, arranged according to certain geometric requirement, and if the conversion unit is provided with a novel charge also containing microorganisms arranged in a suitable environment, and if it connected also in a novel way to the other structural elements of the device, then the arrangement set up in this way consisting of simple structural elements that may be easily constructed collects the electromagnetic radiation much more efficiently and then transforms it, neutralises it with the help of the charge, through which, despite its simpler structure and small component requirement, it is capable of providing greater and more efficient protection against radiation to the area in question and so the task may be solved.

In accordance with the set aim the energy conversion device according to the invention,—which contains one or more collection units suitable for receiving environmental energy as well as a conversion unit in an electrically conducting connection with the collection unit with the help of a cable, at least one of the collection units is formed by a set of metal material pipe members, while the conversion unit has a condenser part-unit consisting of metal armoured plates separated from each other by a gap and located in the cover, as well as a frequency-setting part-unit cooperating with the condenser part-unit, where the frequency-setting part-unit has a reception space located within the cover of the conversion unit and enclosed by a delimiting shell in the vicinity of the condenser part-unit and a charge located in the reception space, and the charge contains an organic component and an inorganic component distributed in a carrier medium,—is set up in such a way that the cable connecting the collection unit and the conversion unit to each other is made from a metal alloy containing a maximum of 0.7 mass % gold, a maximum of 0.7 mass % silver, between 2-8 mass % iron and at least 90 mass % bronze components, and the cable has at least two bending zones, where the normal to the initial section of the cable entering the bending zone and the normal to the exit section of the cable leaving the bending zone are at an angle of at least 10° to each other, the organic component of the charge contains a maximum of 50 v/v % regenerating type microorganism group, while the inorganic component of the charge contains at least 5 v/v % of a gold-bronze powder mixture, the condenser part-unit is connected to an earth cable, and when the device is in its use position the first armoured plate of the condenser part-unit is connected to the electrically conducting body belonging to the environment via the earth cable when the energy conversion device is in its use position, and the second armoured plate of the condenser part-unit, beside the cable, is in an electrically conducting connection with the charge.

A further feature of the energy conversion device according to the invention may be that the carrier medium of the charge is a post-hardening material.

From the point of view of the invention it may be favourable if the carrier medium of the charge contains beeswax.

In the case of another version of the energy conversion device the normal to the initial section of the cable entering the bending zone and the normal to the exit section of the cable leaving the bending zone are at an angle of at least 90° to each other, and in this way with the cable bent in an angular "U" shape it is led between the collection unit and the conversion unit.

In the case of another, different embodiment of the invention an intermediate cable is connected to the cable between the two neighbouring bending zones of the cable.

In the case of yet another different embodiment of the energy conversion device the regenerating type microorganism group belonging to the organic component of the charge contains photosynthesising bacteria and/or lactic acid bacteria and/or yeasts and/or actinomycetes and/or fermenting fungi.

The energy conversion device according to the invention has numerous advantageous characteristics. The most important of these is that due to the novel conversion unit and the unique composition cable connected to it the damaging electromagnetic radiation in the given protected area may be much more efficiently collected and terminated by being converted for useful purposes than what could be achieved with the help of the known versions.

A further advantage is that due to the unique connection arrangement the energy conversion device according to the invention is built from a small number of components, which, beside taking up a minimal amount of space, may exert its advantageous effect and create a positive environment in the area where installed.

Another feature that may be listed among the advantages is that the solution does not demand any change being made to the structure of the building, therefore it may be implemented quickly, with a small amount of physical work being invested. Also as the elements of the device essentially exert their effect in a self-operating way the device does not require maintenance, and it becoming faulty—except for intentional damage—is essentially excluded.

Another feature that must be viewed as an advantage is that an external, active energy source, electricity to be precise, is not required for the operation of the energy conversion device according to the invention, therefore it may be installed in any required location.

Also to be treated as an important advantage is that due to the special composition cable and the novel conversion unit the energy conversion device according to the invention makes it possible to sustain radiation in the frequency range useful for living organisms and so may create even more favourable and healthy conditions for those living and active in the protected environment.

The energy conversion device according to the invention is presented in the following in more detail in connection with embodiments, on the basis of a drawing. In the drawing FIG. 1 shows the outline view picture of a possible version of the energy conversion device in partial cross-section.

In FIG. 1 a version of the energy conversion device according to the invention may be seen that is located along the space delimiting elements 1a of a building section 1. It may be observed that the collection unit 10 is arranged along one of the space delimiting elements 1a of the building section 1 near to a corner while the conversion unit 30 is arranged along another space delimiting element 1a of the building section 1 opposite the first space delimiting element 1a near to a corner. Here the collection unit 10 consists of pipe members 11 lined up next to one another made from an electrically conducting material, e.g. stainless steel and of a housing 12 containing the pipe members 11. Preferably the pipe members 11 consist of pipes eight centimeters in diameter and one meter high, and are lined up next to one another in the housing 12, preferably in two lines so that the longitudinal axes of the pipe members 11 are in a vertical position. The individual pipe members 11 are in an electrically conducting connection with one another.

The conversion unit 30 contains the rectangular prism-shaped condenser part-unit 32 located in the cover 31 as well as the frequency-setting part-unit 33. The condenser part-unit 32 is established from the first armoured plate 32a and from the second armoured plate 32a' located at a distance "T" from it. The frequency-setting part-unit 33 includes the charge 40 in such a way that a part of the charge 40 is located in the reception space 35 in the cover 31 and formed in the carrier medium 36 also encompassing the armoured plates 32a of the condenser part-unit 32 and encompassed by the delimiting shell 34.

The organic component of the charge 40 contains at the most 50 v/v % regenerating type microorganism group, in this case photosynthesising bacteria and/or lactic acid bacteria and/or yeasts and/or actinomycetes and/or fermenting fungi, while the inorganic component of the charge 40 contains at least 5 v/v % of a gold-bronze powder mixture. Here the carrier medium 36 located in the cover 31 of the conversion unit 30 is beeswax, which, in a given case may include a similar composition to the inorganic component of the charge 40, e.g. 5 v/v % of a gold-bronze powder mixture.

Here it must be noted that the ratio between the inorganic and organic components of the charge 40 and the ratio between the photosynthesising bacteria, the lactic acid bacteria, the yeasts, the actinomycetes and the fermenting fungi forming the microorganism group forming the organic component in all cases depends on the originally measured amount of damaging radiation between the space delimiting elements 1a of the building section 1.

FIG. 1 also illustrates that the conversion unit 30 is set up in such a way that the first armoured plate 32a located within the cover 31 is connected to the earth cable 50 in an electrically conducting way, while the second armoured plate 32a' is connected to the cable 20 in an electrically conducting way and also connected to the charge 40 in an electrically conducting way.

The electrically conducting connection between the armoured plate 32a' and the charge 40 located in the reception space 35 delimited by the delimiting shell 34 may also be realised by, for example, the metal mixture containing 5 v/v % gold-bronze embedded in the beeswax used as the carrier medium 36.

The cable 20 connecting the pipe members 11 of the collection unit 10 with the armoured plate 32a' of the condenser part-unit 32 of the conversion unit 300 are arranged along the space delimiting elements 1a of the building section 1 in such a way that—in this case—they are bent into a "U" shape. The cable 20 starting from the housing 12 of the collection unit 10 runs in a straight line along the space delimiting element 1a until it reaches the corner 1b established at the meeting of the first space delimiting element 1a and of the neighbouring second space delimiting element 1a of the building section 1. Here the initial section 21 of the cable 20 enters the bending zone 23 where it bends and leaves the bending zone 23 through the exit zone 22. In this case the normal 21a of the initial section 21 of the cable 20 is at an angle "α" of 90° to the normal 22a of the exit zone 22 of the cable 20. Following this the cable 20 progresses along the next space delimiting element 1a until the next corner 1b, where—similarly to the previous case—it reaches the next bending zone 23, then the initial section 21 after the bending zone 23 continues its path in the exit zone 22. Also in this case a perpendicular angle "α" is established between the normal 21a of the initial section 21 and the normal 22a of the exit zone 22. Finally the cable following the last, in this case second bending zone 23 and following the given space delimiting element 1a arrives at the conversion unit 30 and is connected to the armoured plate 32a' of the condenser part-unit 32.

Here we must note that in all cases the cable 20 must be located so that it does not form a loop in the building section 1 to be protected, and if possible it should run in a "U" shape. However, in the case that the two essentially parallel legs of the "U" shape are located at a distance of more than ten meters from each other, then an intermediate cable 25 must be inserted between the neighbouring bending zones 23—depending on the geometrical form of the base area of the building section 1 encompassed by the space delimiting elements 1a—in such a way that the connection point 24 connecting the intermediate cable 25 with the cable 20 is in the part between the two bending zones 23 of the cable. In this case it is appropriately ensured that the collection of the damaging electromagnetic radiation in the building section 1 to be protected is carried out appropriately.

The cable 20 is made of an electrically conducting material, however, from the point of view of its composition it is unique, as it is made from a metal alloy containing a maximum of 0.7 mass % gold, a maximum of 0.7 mass % silver, between 2-8 mass % iron and at least 90 mass % bronze. As a consequence of the unique alloy the impedance and loss of the cable 20 is between such limits that do not prevent, what is more, that even promote the collection of the damaging electromagnetic radiation and its transmission to the conversion unit 30.

On FIG. 1 it may also be seen that the one armoured plate 32a of the condenser part-unit 32 of the conversion unit 30 is connected to the earth cable 50 in such a way that it is connected to the earth potential of the building section 1.

When using the energy conversion device according to the invention first of all the extent of the various forms of damaging radiation must be measured in the case of the building section 1 to be protected, then the condenser part-unit 32 and the unique conversion unit 30 including the charge 40 must be established in accordance with the value obtained. Following this, following the positioning of the collection unit 10 and the conversion unit 30 these must be connected to the cable 10, whilst the cable 20 is appropriately positioned and possibly the intermediate cable 25 is connected to the connection point 24. Finally the first armoured plate 32a of the condenser part-unit 32 of the conversion unit 30 must be connected to the earth potential of the building section 1 with the help of the earth cable 50.

During the operation of the energy conversion device the pipe members 11 of the collection unit 10 and the cable 20 collect the electromagnetic radiation arriving into the building section 1, and then this is forwarded to the condenser part-unit 32 of the conversion unit 30 via the cable 20. The energy accumulated in the condenser part-unit 32 gets to the charge 40 electrically connected to the armoured plate 32a of the condenser part-unit 32 where the organic components forming the charge 40 use it for the operation of their lives, terminating with this the energy arriving in the damaging radiation range.

The energy conversion device according to the invention may be used to good effect in all places where effective protection must be ensured against electromagnetic radiation arriving from the environment and a simple, quickly implementable and reliably operating solution is required.

The invention claimed is:

1. An energy conversion device which contains at least one collection unit suitable for receiving environmental energy as well as a conversion unit in an electrically conducting connection with the collection unit by means of a cable, said at least one collection unit being formed by a set of metal material pipe members, the conversion unit having a condenser part-unit comprising metal armoured plates separated from each other by a gap and located in a cover of the conversion unit, as well as a frequency-setting part-unit cooperating with the condenser part-unit;

wherein the frequency-setting part-unit has a reception space located within the cover of the conversion unit and enclosed by a delimiting shell in a vicinity of the condenser part-unit and a charge located in the reception space, the charge containing an organic component and an inorganic component distributed in a carrier medium;

wherein the cable connecting the collection unit and the conversion unit to each other is made from a metal alloy containing a maximum of 0.7 mass % gold, a maximum of 0.7 mass % silver, between 2 and 8 mass % iron, and at least 90 mass % bronze components, and wherein the cable has at least two bending zones, a normal to an initial section of the cable entering the bending zone and a normal to an exit section of the cable leaving the bending zone being at an angle (a) of at least 10° to each other; and wherein the organic component of the charge contains a maximum of 50 v/v % regenerating type microorganism group, while the inorganic component of the charge contains at least 5 v/v % of a gold-bronze powder mixture, the condenser part-unit being connected to an earth cable, and wherein a first armoured plate of the condenser part-unit is connected to an electrically conducting body belonging to the environment via the earth cable when the energy conversion device is in a use position, and a second armoured plate of the condenser part-unit, beside the cable, is in an electrically conducting connection with the charge.

2. The energy conversion device according to claim 1, wherein the carrier medium of the charge is a post-hardening material.

3. The energy conversion device according to claim 2, wherein the carrier medium of the charge contains beeswax.

4. The energy conversion device according to claim 3, wherein the normal to the initial section of the cable entering the bending zone and the normal to the exit section of the cable leaving the bending zone are at an angle (α) of 90° relative to each other, and in this way, with the cable being bent in an angular "U" shape, the cable is led between the collection unit and the conversion unit.

5. The energy conversion device according to claim 4, wherein an intermediate cable is connected to the cable between said at least two neighboring bending zones of the cable.

6. The energy conversion device according to claim 5, wherein the regenerating type microorganism group belonging to the organic component of the charge contains at least one of photosynthesising bacteria, lactic acid bacteria, yeasts, actinomycetes and fermenting fungi.

7. The energy conversion device according to claim 2, wherein the normal to the initial section of the cable entering the bending zone and the normal to the exit section of the cable leaving the bending zone are at an angle ($\alpha$) of 90° relative to each other, and in this way, with the cable being bent in an angular "U" shape, the cable is led between the collection unit and the conversion unit.

8. The energy conversion device according to claim 2, wherein an intermediate cable is connected to the cable between said at least two neighboring bending zones of the cable.

9. The energy conversion device according to claim 1, wherein the carrier medium of the charge contains beeswax.

10. The energy conversion device according to claim 9, wherein the normal to the initial section of the cable entering the bending zone and the normal to the exit section of the cable leaving the bending zone are at an angle ($\alpha$) of 90° relative to each other, and in this way, with the cable being bent in an angular "U" shape, the cable is led between the collection unit and the conversion unit.

11. The energy conversion device according to claim 10, wherein an intermediate cable is connected to the cable between said at least two neighboring bending zones of the cable.

12. The energy conversion device according to claim 11, wherein the regenerating type microorganism group belonging to the organic component of the charge contains at least one of photosynthesising bacteria, lactic acid bacteria, yeasts, actinomycetes and fermenting fungi.

13. The energy conversion device according to claim 9, wherein an intermediate cable is connected to the cable between said at least two neighboring bending zones of the cable.

14. The energy conversion device according to claim 1, wherein the normal to the initial section of the cable entering the bending zone and the normal to the exit section of the cable leaving the bending zone are at an angle ($\alpha$) of 90° relative to each other, and in this way, with the cable being bent in an angular "U" shape, the cable is led between the collection unit and the conversion unit.

15. The energy conversion device according to claim 14, wherein an intermediate cable is connected to the cable between said at least two neighboring bending zones of the cable.

16. The energy conversion device according to claim 15, wherein the regenerating type microorganism group belonging to the organic component of the charge contains at least one of photosynthesising bacteria, lactic acid bacteria, yeasts, actinomycetes and fermenting fungi.

17. The energy conversion device according to claim 14, wherein the regenerating type microorganism group belonging to the organic component of the charge contains at least one of photosynthesising bacteria, lactic acid bacteria, yeasts, actinomycetes and fermenting fungi.

18. The energy conversion device according to claim 1, wherein an intermediate cable is connected to the cable between said at least two neighboring bending zones of the cable.

19. The energy conversion device according to claim 18, wherein the regenerating type microorganism group belonging to the organic component of the charge contains at least one of photosynthesising bacteria, lactic acid bacteria, yeasts, actinomycetes and fermenting fungi.

20. The energy conversion device according to claim 1, wherein the regenerating type microorganism group belonging to the organic component of the charge contains at least one of photosynthesising bacteria, lactic acid bacteria, yeasts, actinomycetes and fermenting fungi.

* * * * *